United States Patent [19]

Roses et al.

[11] Patent Number: 5,767,248

[45] Date of Patent: Jun. 16, 1998

[54] APOLIPOPROTEIN E ISOFORM-SPECIFIC MONOCLONAL ANTIBODIES

[75] Inventors: Allen D. Roses; Warren J. Strittmatter, both of Durham; Guy S. Salvesen. Chapel Hill; Jan Enghild; Donald E. Schmechel, both of Durham, all of N.C.

[73] Assignee: Duke University, Durham, N.C.

[21] Appl. No.: 835,503

[22] Filed: Apr. 8, 1997

Related U.S. Application Data

[60] Continuation of Ser. No. 440,900, May 15, 1995, abandoned, which is a division of Ser. No. 227,044, Apr. 13, 1994, Pat. No. 5,508,167, which is a continuation-in-part of Ser. No. 114,448, Aug. 31, 1993, abandoned, which is a continuation-in-part of Ser. No. 959,992, Oct. 13, 1992, abandoned.

[51] Int. Cl.$^6$ ............................................. C07K 16/00
[52] U.S. Cl. ........................... 530/388.25; 530/387.9; 530/388.1; 530/391.1; 530/391.3
[58] Field of Search ........................... 530/387.9, 388.1, 530/388.25, 391.1, 391.3

[56] References Cited

U.S. PATENT DOCUMENTS 5,168,045 12/1992 Dyer et al.
5,272,055 12/1993 Haley.
5,297,562 3/1994 Potter.

FOREIGN PATENT DOCUMENTS

WO 92/10512 6/1992 WIPO.

OTHER PUBLICATIONS

Joachim et al.; "Antibodies to Non–beta Regions of the Beta–amyloid Precursor Protein Detect a Subset of Senile Plaques"; *Amer. J. Pathology,* 138:373–384 (1991).

G.C. Glenner and C.W. Wong; Alzheimer's Disease: Initial Report of the Purification and Characterization of a Novel Cerebrovascular Amyloid Protein, *Biochemical and Biophysical Research Communications* 120 pp. 885–890 (1984).

G.D. Schellenberg, et al; Association of an apolipoprotein CII allele with familial dementia of the Alzheimer type, *Journal of Neurogeneics* 4, pp. 97–108 (1987).

M. Emi, et al; Genotyping and Sequence Analysis of Apolipoprotein E Isoforms, *Genomics 3,* pp. 373–379 (1988).

A. Steinmetz et al; Confusion of Apolipoprotein E Phenotyping by Serum Amyloid A., *Clin Chem* 35, pp. 671–672 (1989).

H. Shimano, et al; Plasma apolipoproteins in patients with multi–infarct dementia, *Atheroscierosis* 79, pp. 257–260 (1989).

H. Maeda et al; Identification of Human Apolipoprotein E Variant Gene: Apolipoprotein E7 ($Glu_{244, 245}$–$LYS_{244, 245}$), *The Journal of Biochemistry* 105 No. 1, pp. 51–54 (1989).

J.E. Hixson et al; Restriction isotyping of human apolipoprotein E by gene amplification and cleavage with HhaI, *Journal of Lipid Research* 31, pp. 545–548 (1990).

K. Kontula et al; Apotipoprotein E Polymorphism Determined by Restriction Enzyme Analysis of DNA Amplified by Polymerase Chain Reaction: Convenient Alternative to Phenotyping by Isoelectric Focusing, *Clin. Chem* 36, pp. 2087–2092 (1990).

D.J. Selkoe; The Molecular Pathology of Alzheimer's Disease, *Neuron* 6 pp. 487–498 (1991).

F. Wiederkehr; Analysis of cerebrospinal fluid proteins by electrophoresis; *Journal of Chromatography* 569 pp. 281–296 (1991).

P. Wenham et al; Apolipoprotein E genotyping by one–stage PCR, *The Lancet* 337, pp. 1158–1159 (1991).

M.A. Pericak–Vance, et al; Linkage Studies in Familial Alzheimer Disease: Evidence for Chromosome 19 Linkage; *Am. J. Hum. Genet.,* 48 pp. 1034–1050 (1991).

Y. Namba et al; Apolipoprotein E. immunoreactivity in cerebral amyloid deposits and neurofibrillary tangles in Alzheimer's disease and kuru plaque amyloid in Creutzfield–Jakob disease: *Brain Res.* 541, pp. 163–166 (1991).

J.F. Diedrich, et al; Neuropathological Changes in Scrapie and Alzheimer's Disease are Associated with Increased Expression of Apolipoprotein E and Cathepsin D in Astrocytes; *Jounal of Virology* pp. 4759–4768 (1991).

K. Beyreuther and C.L. Masters. Amyloid Precursor Protein (APP) and βA4 Amyloid in the Etiology of Alzheimer's Disease: Precursor–Product Relationships in the Derangement of Neuronal Function; *Brain Pathology* 1, pp. 241–251 (1991).

F. Tagliavini, et al; Alzheimer patients: preamyloid deposits are immunoreactive with antibodies to extracellular domains of the amyloid precursor protein; *Neuroscience Letters 128,* pp. 117–120 (1991).

C. Joachim, et al; Antibodies to Non–beta Regions of the Beta–amyloid Precursor Protein Detect a Subset of Senile Plaques; *American Journal of Pathology* 138 pp. 373–384 (1991).

K.S. Kosik; Alzheimer's Disease: A Cell Biological Perspective, *Science* 256, pp. 780–783 (1992).

J. Hardy; Genetic Mistakes Point the Way for Alzheimer's Disease, *The Journal of NIH Research* 5, pp. 46–49 (1993).

(List continued on next page.)

*Primary Examiner*—Paula K. Hutzell
*Assistant Examiner*—Patricia A. Duffy
*Attorney, Agent, or Firm*—Myers Bigel Sibley & Sajovec, PA

[57] ABSTRACT

Methods of diagnosing or prognosing Alzheimer's disease in a subject are disclosed. The methods involve directly or indirectly detecting the presence or absence of an apolipoprotein E type 4 (ApoE4) isoform or DNA encoding ApoE4 in the subject. The presence of ApoE4 indicates the subject is afflicted with Alzheimer's disease or at risk of developing Alzheimer's disease. A novel immunochemical assay for detecting the presence or absence of the Apoliprotein E (ApoE) E4 allele in a subject is also disclosed.

6 Claims, 4 Drawing Sheets

OTHER PUBLICATIONS

W.J. Strittmatter, et al; Apolipoprotein E: High–avidity binding to β–amyloid and increased frequency of type 4 allele in late–onset familial Alzheimer disease; *Proc. Natl. Acad. Sci.* 90, pp. 1977–1981 (1993).

C. Zarow anc C.E. Finch; *Abstract Apolipoprotein E Expression in Alzheimer's Disease and after Hippocampal Deafferentation in the Rat*.

A.M. Saunders et al; Association of apolipoprotien E allel ε4 with late–onset familial and sporadic Alzheimer's disease, *Neurology* 43, pp. 1467–1472 (1993).

J. Travis, New Piece in Alzheimer's Puzzle, *Science* 261, pp. 828–829 (1993).

A.M. Saunders, et al; Apolipoprotein E ε4 allele distributions in late–onset Alzheimer's disease and in other amyloid–forming diseases, *The Lancet* 342, pp. 710–711 (1993).

J. Poirier, et al; Apolipoprotein E polymorphism and Alzheimer's disease, *The Lancet* 342, pp. 697–699 (1993).

W.J. Strittmatter et al; Binding of human apolipoprotein E to synthetic amyloid β peptide: Isoform–specific effects and implications for late–onset Alzheimer's disease, *Proc. Natl. Acad. Sci.* 90, pp. 8098–8102 (1993).

D.E. Schmechel, et al; Increased amyloid β–peptide deposition in cerebral cortex as a consequence of apolipoprotein E genotype in late–onset Alzheimer disease, *Proc. Natl. Acad. Sci.* 90, pp. 9649–9653 (1993).

E.H. Corder, et al; Gene Dose of Apolipoprotein E Type 4 Allele and the Risk of Alzheimer's Disease in Late Onset Families, *Science* 261, pp. 921–923 (1993).

M. Waldholz, Clue to a Killer Alzheimer's is Linked to the Way the Blood Transports Cholesterol, *Wall Street Journal* Jun. 7, 1993.

A. Toufexis, Alzheimer's Clue: Once ignored, a scientist gains support for his idea that a common gene helps cause the disease, *Time* Jun. 21, 1993.

R. Mayeux, et al; The Apolipoprotein ε4 Allele in Patients with Alzheimer's Disease, *Annal of Neurology* 34; pp. 752–754, Nov. 1993.

Neurology Notes, Announcing the New ApoE GenoType Report, *Genica Pharmaceuticals Corp.* (1993).

A. Roses; The Alzheimer Diseases, *Current Neurology* 14, pp. 111–141 (1994).

G. Lucotte, et al; Apolipoprotein E–ε4 Allele Doses in Late–Onset Alzheimer's Disease, *Annals of Neurology* 36 No. 4, pp. 681–682 (1994).

L. Lannfelt, et al; Lack of Association between apolipoprotein E allele ε4 and sporadic Alzheimer's disease, *Neuroscience Letters* 169 pp. 175–178 (1994).

T. Yoshizawa, et al; Dose–dependent Association of Apolipoprotein E Allele ε4 with Late–Onset, Sporadic Alzheimer's Disease, *The American Neurological Association* 36, No. 4, pp. 656–659 (1994).

P. Amouyel, et al; The Apolipoprotein E alleles as major susceptibility factors for Creutzfeldt–Jakob disease, *The Lancet* 344, pp. 1315–1318 (1994).

W.A. Kukull; *Revision of reported APOE results*, (Nov. 3, 1994)

Gerritse et al (1992) J. Lipid Res. 33:273–280. (Feb. issue).

Harlow et al. (1988) "Antibodies: A Laboratory Manual," Cold Spring Harbor Press, Cold Spring Harbor, N.Y., pp. 553–612 and 321–358.

5,767,248

APOLIPOPROTEIN E ISOFORM-SPECIFIC MONOCLONAL ANTIBODIES

This application is a File Wrapper Continuation of U.S. patent application Ser. No. 08/440,990, filed May 15, 1995, now abandoned which is a divisional of U.S. patent application Ser. No. 08/227,044, filed Apr. 13, 1994, now U.S. Pat. No. 5,508,167, which is a continuation-in-part of U.S. patent application Ser. No. 08/114,448, filed Aug. 31, 1993, now abandoned which is a continuation-in-part of U.S. patent application Ser. No. 07/959,992, filed Oct. 13, 1992, now abandoned the disclosures of which applications are all incorporated herewith in their entirety.

This invention was made with Government support under NIH LEAD Award 5R35 AGO 7922 and NIH Alzheimer's Disease Research Center 5P50 AGO 5128. The Government has certain rights to this invention.

FIELD OF THE INVENTION

The present invention relates to methods of diagnosing and prognosing Alzheimer's disease. The invention further includes immunological methods of distinguishing various isoforms of apolipoprotein E (ApoE), and particularly for distinguishing ApoE4 from ApoE2 and ApoE3.

BACKGROUND OF THE INVENTION

The senile plaque and congophilic angiopathy are abnormal extracellular structures found in abundance in brain of patients with Alzheimer's disease. The biochemical composition of these structures has been extensively studied to better understand their possible role in the pathogenesis of this dementing disease. The mature senile plaque is a complex structure, consisting of a central core of amyloid fibrils surrounded by dystrophic neurites, axonal terminals and dendrites, microglia and fibrous astrocytes. See D. Selkoe *Neuron* 6, 487–498 (1991). The amyloid core of the senile plaque surrounding blood vessels, producing the congophilic angiopathy, is a peptide of 39 to 43 amino acids termed the β-Amyloid (Aβ) peptide. G. Glenner and C. Wong, *Biochem. Bioshys. Res. Comm.* 120, 885–890 (1984). Aβ peptide is found in brain in Alzheimer's disease, Down's syndrome, hereditary cerebral hemorrhage of the Dutch type, and in old age. K. Kosik, *Science* 256, 780–783 (1992). Aβ is produced by abnormal proteolytic processing of a larger protein, the amyloid precursor protein (APP). See K. Bayreuther and C. Masters, *Brain Path.* 1, 241–251 (1991).

The senile plaque and congophilic angiopathy contain proteins in addition to βA peptide. APP itself, among others, has been identified in the senile plaque by histochemical studies employing antibodies recognizing either the amino- and carboxy- termini of the precursor protein. See, e.g., F. Tagliavine et al., *Neurosci. Lett.* 128, 117–120 (1991); C. Joachim et al., *Amer. Jour. Path.* 138, 373–384 (1991); The mechanisms by which these proteins aggregate in the extracellular space to associate with the senile plaque and congophilic angiopathy are not known.

Apolipoprotein E (ApoE) performs various functions as a protein constituent of plasma lipoproteins, including its role in cholesterol metabolism. It was first identified as a constituent of liver-synthesized very low density lipoproteins which function in the transport of triglycerides from the liver to peripheral tissues. There are three major isoforms of ApoE, referred to as ApoE2, ApoE3 and ApoE4 which are products of three alleles at a single gene locus. Three homozygous phenotypes (Apo-E2/2, E3/3, and E4/4) and three heterozygous phenotypes (ApoE3/2, E4/3 and E4/2) arise from the expression of any two of the three alleles. The most common phenotype is ApoE3/3 and the most common allele is E3. See Mahley, R. W., *Science* 240:622–630 (1988).

The amino acid sequences of the three types differ only slightly. ApoE4 differs from ApoE3 in that in ApoE4 arginine is substituted for the normally occurring cysteine at amino acid residue 112. The most common form of ApoE2 differs from ApoE3 at residue 158, where cysteine is substituted for the normally occurring arginine. See Mahley, *Science*, supra.

While there has been considerable research into the mechanisms underlying Alzheimer's disease, there continues to be an ongoing need for new ways to investigate and combat this disorder.

SUMMARY OF THE INVENTION

Methods of diagnosing or prognosing Alzheimer's disease in a subject are disclosed. One embodiment comprises detecting the presence or absence of DNA encoding an apolipoprotein E type 4 (ApoE4) isoform in the subject. Another embodiment comprises detecting the presence or absence of an ApoE4 isoform. The presence of an ApoE4 isoform or of DNA encoding an ApoE4 isoform indicates that the subject is afflicted with Alzheimer's disease or at risk of developing Alzheimer's disease. Kits for diagnosing or prognosing Alzheimer's disease are also described.

The immunochemical assay comprises collecting a sample such as a blood sample from the subject, optionally combining the sample with a reducing agent, contacting the sample to a solid support which specifically binds reactive sulfhydryl groups, then separating the sample from the solid support, and then detecting by immunoassay either (i) the presence or absence of ApoE in said sample, the presence of ApoE in said sample indicating the subject has at least one allele for ApoE4, the absence of ApoE in said sample indicating said subject has no alleles for ApoE4, or (ii) the presence or absence of ApoE immobilized on the solid support, the presence of ApoE immobilized on said solid support indicating said subject has one or no alleles for ApoE4, the absence of ApoE immobilized on the solid support indicating said subject has two alleles for ApoE4.

A further aspect of the present invention is a kit useful for detecting the presence of the ApoE4 allele in a subject by immunochemical assay. The kit comprises a solid support which specifically binds reactive sulfhydryl groups, and antibodies which specifically bind ApoE.

A simple test is provided to determine whether an individual has the ApoE4 isoform, and whether the individual is homozygous for ApoE4 (i.e. produces only ApoE4) or is heterozygous for ApoE4 (i.e. produces ApoE4 and an additional isoform of ApoE). The test is based on the differences in the amino acid sequences of the three major ApoE isoforms, ApoE2, ApoE3, and ApoE4. ApoE4 contains no cysteines, ApoE3 contains one cysteine, and ApoE2 contains two cysteines. By relying on chemical means for distinguishing among the different ApoE isoforms, the problem of potential cross-reactivity of antibodies used to carry out the immunoassay with multiple ones of the isoforms is obviated.

The foregoing and other objects and aspects of the present invention are explained in detail in the specification set forth hereinbelow.

DETAILED DESCRIPTION OF THE INVENTION

Figure 1:
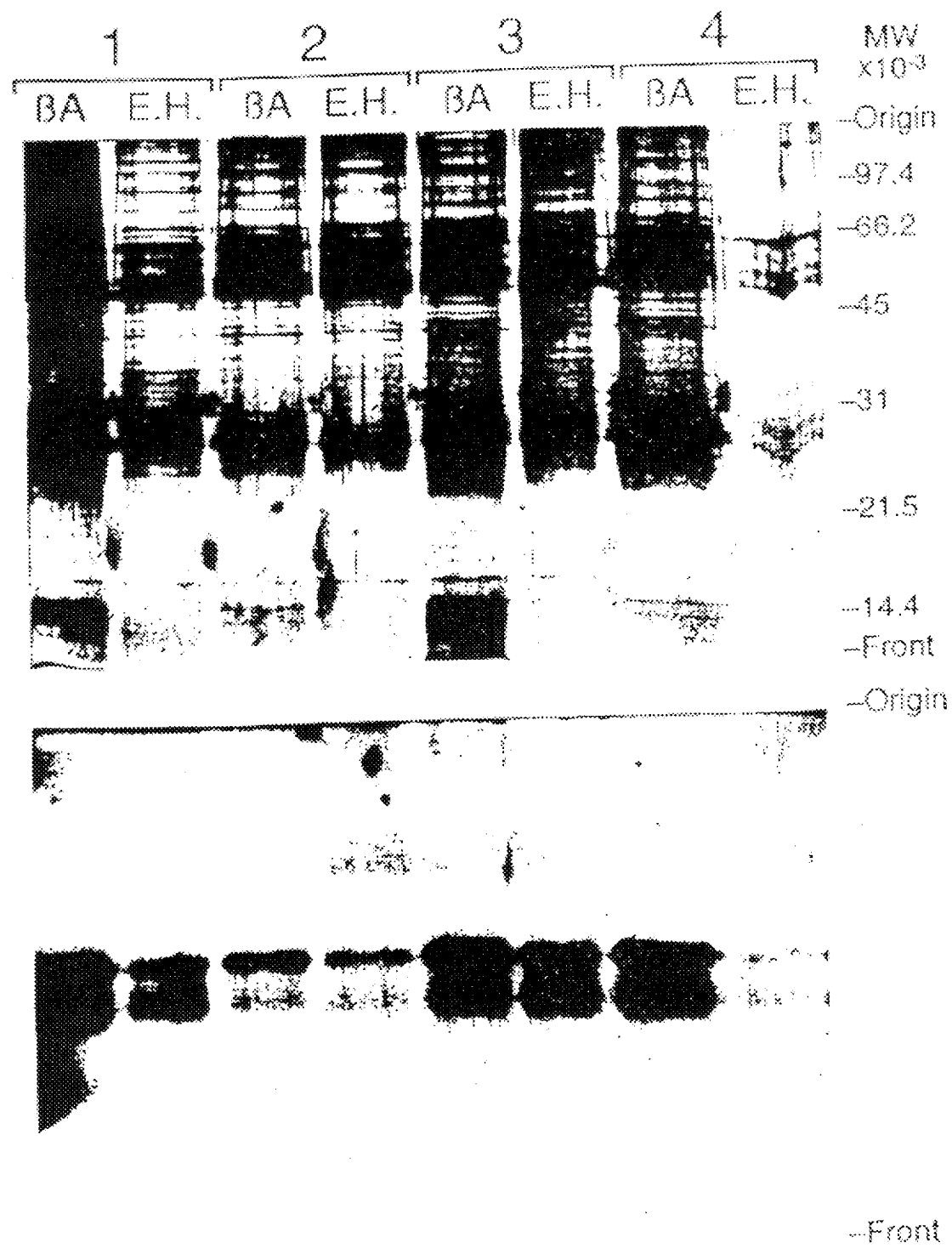
FIG. 1, top panel, shows proteins in cerebrospinal fluid which bind to immobilized βA peptide, and to a control peptide (the "even-hydro peptide", or "E.H.") after incubation and: elution with phosphate buffered saline, column 1; elution with 5% sodium dodecyl sulfate, column 2; elution with 4 molar urea, column 3; or elution with 6 molar guanidine hydrochloride, column 4. Binding of Apolipoprotein E is shown by immunohistochemical staining in the bottom panel.

As noted above, the present invention provides a method of screening (e.g., diagnosing or prognosing) for Alzheimer's disease in a subject. The method comprises detecting the presence or absence of ApoE4 isoform or of DNA encoding an ApoE4 isoform in the subject. The presence of such isoform or DNA indicates that the subject is afflicted with Alzheimer's disease or at risk of developing Alzheimer's disease. Suitable subjects include those which have not previously been diagnosed as afflicted with Alzheimer's disease, those which have previously been determined to be at risk of developing Alzheimer's disease, and those who have been initially diagnosed as being afflicted with Alzheimer's disease where confirming information is desired. For example, patients diagnosed or determined to be afflicted with dementia, particularly patients who had previously been clinically normal who are determined to be afflicted with a progressive dementia, are suitable subjects. Thus, the present invention may be employed in detecting both familial Alzheimer's disease (late onset and early onset) as well as sporadic Alzheimer's disease. Many Alzheimer's disease patients encountered in practice have no obvious family history and have been classified as sporadic. However, genetic factors in early—and late—onset of familial Alzheimer's disease (FAD) are well documented. Late-onset Alzheimer's disease is the classification usually used if the disease is diagnosed to occur after the age of 65 in humans.

Observing whether or not the ApoE4 isoform of ApoE is present or absent in a subject enables one to observe or determine whether or not a subject is afflicted with or at increased risk of developing Alzheimer's disease. Affliction with the disease is more likely if ApoE4 is present. A subject with ApoE4 is at increased risk of developing Alzheimer's disease over subjects in which ApoE4 is absent. A subject who is "at increased risk of developing Alzheimer's disease" is one who is predisposed to the disease, has genetic susceptibility for the disease or is more likely to develop the disease than subjects in which ApoE4 is absent.

Further, the methods of the present invention can be used to aid in determining the prognosis of a subject afflicted with or at risk for Alzheimer's disease based on the observation of how many alleles for ApoE4 are detected in the subject. The subject's prognosis is more negative if the presence of ApoE4 is detected than if it is absent; the subject's prognosis is most negative if the presence of more than one allele for ApoE4 is detected.

For example, subjects with the ApoE4/4 genotype are as much as eight times as likely to be affected by Alzheimer's disease as subjects with the ApoE2/3 or ApoE3/3 genotypes. Further, the average age of onset of Alzheimer's disease and the average age of survival is younger for those having one ApoE4 allele, and youngest for those having two ApoE4 alleles. Thus, a subject's prognosis for Alzheimer's disease is more likely to be negative if the subject has an ApoE4 allele and most negative if the subject has more than one ApoE4 allele. The negative prognosis can be viewed in terms of increased likelihood of developing the disease, or of increased likelihood of developing the disease or dying at an earlier age.

It is preferred and contemplated that the methods described herein be used in conjunction with other clinical diagnostic information known or described in the art which are used in evaluation of subjects with Alzheimer's disease or suspected to be at risk for developing such disease.

ApoE phenotypes and genotypes are well described and known in the art as described above. The established nomenclature system as well as the phenotypes and genotypes for ApoE, are described in, for example, Zannis et al., *J. Lipid. Res.* 23:911 et seq. (1982), which is incorporated by reference herein.

The step of detecting the presence or absence of ApoE4 or of DNA encoding such isoform (including the number of alleles for ApoE4) may be carried out either directly or indirectly by any suitable means. A variety of techniques are known to those skilled in the art. All generally involve the step of collecting a sample of biological material containing either DNA or ApoE from the subject, and then detecting whether or not the subject possesses ApoE4 or DNA encoding such isoform from that sample. For example, the detecting step may be carried out by collecting an ApoE sample from the subject (for example, from cerebrospinal fluid, or any other fluid or tissue containing ApoE), and then determining the presence or absence of an ApoE4 isoform in the ApoE sample (e.g., by isoelectric focusing or immunoassay).

The isolation and characterization of ApoE is described, for example, in Rall et al., *Methods in Enzymology* 128:273–287 (1986), Davignon et al., *Arteriosclerosis* 8:1–21 (1988), and in Warnick et al., *Clin. Chem.* 25:279–284 (1979), all of which are incorporated by reference herein. Isoelectric focusing is an electrophoretic technique by which the molecules are separated based on their isoelectric points (pI) along a continuous pH gradient. Reference proteins, commercially available (e.g., Sigma Chemical Company, St. Louis, Mo.), are used to indicate a gradient along which the sample proteins match up according to where their pH matches their pI. In Warnick, et al. very-low-density apolipoproteins are isolated from plasma samples and applied to isoelectric focusing gels and the isoelectric focusing patterns of the ApoE isoforms are obtained. According to the Warnick et al. procedure, pI values of the ApoE isoforms, E2, E3 and E4, were about 5.9, 6.0 and 6.1 respectively in 8 M/L urea at 4° C. See also, Pagnan et al., *J. Lipid. Res.* 18:613–622 (1977) and Utermann et al., *FEBS Lett.* 56:352–355 (1975), both of which are incorporated by reference herein. Various isoeletric focusing-type techniques are also provided in Rall et al.

supra, including analytical isoelectric focusing, cysteamine treatment, neuraminidase treatment, sodium dodecyl sulfate-polyacrylamide gel electrophoresis, as well as amino acid analysis and nucleic acid sequence analysis, and capillary isoelectric focusing is described in H. Swartz, Bio/Technology 12, 408–09 (April 1994).

In the alternative, the detecting step may be carried out by collecting a biological sample containing DNA from the subject, and then determining the presence or absence of DNA encoding an ApoE4 isoform in the biological sample. Any biological sample which contains the DNA of that subject may be employed, including tissue samples and blood samples, with blood cells being a particularly convenient source. The amino acid sequences and nucleic acid sequences for ApoE2, ApoE3 and ApoE4 are known and described. See, for example, Paik et al., Proc. Nat'l Acad. Sci. USA 82:3445–3449 (1985), incorporated by reference herein, for the nucleic acid sequence of ApoE3 and ApoE4; and Mahley, Science, supra for the amino acid sequence information.

Determining the presence or absence of DNA encoding an ApoE4 isoform may be carried out with an oligonucleotide probe labelled with a suitable detectable group, or by means of an amplification reaction such as a polymerase chain reaction or ligase chain reaction (the product of which amplification reaction may then be detected with a labelled oligonucleotide probe or a number of other techniques). Further, the detecting step may include the step of detecting whether the subject is heterozygous or homozygous for the gene encoding an ApoE4 isoform. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally D. Kwoh and T. Kwoh, Am. Biotechnol. Lab. 8, 14–25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392–396 (1992); G. Walker et al., Nucleic Acids Res. 20, 1691–1696 (1992)), transcription-based amplification (see D. Kwoh et al., Proc. Natl. Acad Sci. USA 86, 1173–1177 (1989)), self-sustained sequence replication (or "3SR") (see J. Guatelli et al., Proc. Natl. Acad. Sci. USA 87, 1874–1878 (1990)), the Qβ replicase system (see P. Lizardi et al., BioTechnology 6, 1197–1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is currently preferred.

DNA amplification techniques such as the foregoing can involve the use of a probe, a pair of probes, or two pairs of probes which specifically bind to DNA encoding ApoE4, but do not bind to DNA encoding ApoE2 or ApoE3 under the same hybridization conditions, and which serve as the primer or primers for the amplification of the ApoE4 DNA or a portion thereof in the amplification reaction (likewise, one may use a probe, a pair of probes, or two pairs of probes which specifically bind to DNA encoding ApoE2, but do not bind to DNA encoding ApoE3 or ApoE4 under the same hybridization conditions, and which serve as the primer or primers for the amplification of the ApoE2 DNA or a portion thereof in the amplification reaction; and one may use a probe, a pair of probes, or two pairs of probes which specifically bind to DNA encoding ApoE3, but do not bind to DNA encoding ApoE2 or ApoE4 under the same hybridization conditions, and which serve as the primer or primers for the amplification of the ApoE3 DNA or a portion thereof in the amplification reaction).

In general, an oligonucleotide probe which is used to detect DNA encoding ApoE4 is an oligonucleotide probe which binds to DNA encoding ApoE4, but does not bind to DNA encoding ApoE2 or ApoE3 under the same hybridization conditions. The oligonucleotide probe is labelled with a suitable detectable group, such as those set forth below in connection with antibodies. Likewise, an oligonucleotide probe which is used to detect DNA encoding ApoE2 is an oligonucleotide probe which binds to DNA encoding ApoE2 but does not bind to DNA encoding ApoE3 or ApoE4 under the same hybridization conditions, and an oligonucleotide probe which is used to detect DNA encoding ApoE3 is an oligonucleotide probe which binds to DNA encoding ApoE3 but does not bind to DNA encoding ApoE2 or ApoE4 under the same hybridization conditions.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all ApoE allelic types, the types can be distinguished by hybridization with allelic specific probe, by restriction endonuclease digestion, by electrophoresis on denaturing gradient gels, or other techniques. A PCR protocol for determining the ApoE genotype is described in Wenham et al., The Lancet 337:1158–1159 (1991), incorporated by reference herein. Examples of primers effective for amplification and identification of the ApoE isoforms are described therein. Primers specific for the ApoE polymorphic region (whether ApoE4, E3 or E2) can be employed. In Wenham, for example, PCR primers are employed which amplify a 227 bp region of DNA that spans the ApoE polymorphic sites (codons 112 and 158, which contain nucleotides 3745 and 3883). The amplified fragments are then subjected to restriction endonuclease CfoI which provides different restriction fragments from the six possible ApoE genotypes which may be recognizable on an electrophoresis gel. See also, Hixon et al., J. Lipid Res. 31:545–48 (1990); Houlston et al., Hum. Genet. 83:364–365 (1989) Wenham et al., Clin. Chem.

37:241–244 (1991); and Konrula et al., 36:2087–92 (1990) for additional methods, all of which are incorporated by reference herein.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

It will be readily appreciated that the detecting steps described herein may be carried out directly or indirectly. Thus, for example, if either ApoE2 or ApoE3 is also detected in the subject, then it is determined that the subject is not homozygous for ApoE4; and if both ApoE2 and ApoE3 are detected in the subject, then it is determined that the subject is neither homozygous nor heterozygous for ApoE4. Other means of indirectly determining allelic type could be by measuring polymorphic markers that are linked to ApoE allele, as has been demonstrated for the VNTR (variable number tandem repeats) and the ApoB alleles (Decorter et al., *DNA & Cell Biology* 9(6), 461–69 (1990).

As an alternative to isoelectric focusing and techniques for allele detection, the step of determining the presence or absence of the ApoE4 isoform in a sample may be carried out by an antibody assay with an antibody which selectively binds to ApoE4 (i.e., an antibody which binds to ApoE4 but exhibits essentially no binding to ApoE2 or ApoE3 in the same binding conditions). When one wishes to determine the precise ApoE complement of a patient and whether or not that patient is homozygous or heterozygous for ApoE4, then antibodies which selectively bind to ApoE2 and ApoE3 may also be employed (i.e., an antibody which binds to ApoE2 but exhibits essentially no binding to ApoE3 or ApoE4 in the same binding conditions; an antibody which binds to ApoE3 but exhibits essentially no binding to ApoE2 or ApoE4 in the same binding conditions).

Antibodies used to selectively or specifically bind ApoE2, ApoE3, and ApoE4 can be produced by any suitable technique. For example, monoclonal antibodies may be produced in a hybridoma cell line according to the techniques of Kohler and Milstein, *Nature* 265, 495–97 (1975). ApoE2, ApoE3, or ApoE4 may be obtained from a human patient determined to be homozygous therefore, then purified by the technique described in S. Rall et al., *Methods in Enzymol.* 128, 273 (1986), and used as the immunogen for the production of monoclonal or polyclonal antibodies. Purified ApoE isoforms may be produced by recombinant means to express a biologically active isoform, or even an immunogenic fragment thereof may be used as an immunogen. Monoclonal Fab fragments may be produced in *Escherichia coli* from the known sequences by recombinant techniques known to those skilled in the art. See, e.g., W. Huse, *Science* 246, 1275–81 (1989) (recombinant Fab techniques); P. Wenham et al., *Lancet* 337, 1158 (1991) (ApoE PCR primers). The DNA encoding one subtype of ApoE can be obtained and converted to the other by site-directed mutagenesis. See, e.g., T. Kunkel et al., *Methods in Enzymol.* 154, 367–382 (1987); T. Kunkel, U.S. Pat. No. 4,873,192.

The term "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies, and include antibody fragments such as, for example, Fab, F(ab')$_2$, and Fe fragments, and the corresponding fragments obtained from antibodies other than IgG.

For this invention, an antibody selectively or specifically binding ApoE or a particular ApoE isoform (ligand) generally refers to a molecule capable of reacting with or otherwise recognizing or binding such a ligand. An antibody has binding affinity for a ligand or is specific for a ligand if the antibody binds or is capable of binding the ligand as measured or determined by standard antibody-antigen or ligand-receptor assays, for example, competitive assays, saturation assays, or standard immunoassays such as ELISA or RIA. This definition of specificity applies to single heavy and/or light chains, CDRs, fusion proteins or fragments of heavy and/or light chains, that are specific for the ligand if they bind the ligand alone or in combination.

Antibody assays (immunoassays) may, in general, be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention and a system or means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See generally E. Maggio, *Enzyme-Immunoassay,* (1980) (CRC Press, Inc., Boca Raton, Fla.); see also U.S. Pat. No. 4,727,022 to Skold et al. titled "Methods for Modulating Ligand-Receptor Interactions and their Application." U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies which selectively bind an ApoE isoform (i.e., bind to one of ApoE2, ApoE3 or ApoE4 while showing essentially no binding to the other under the same binding conditions) may be conjugated to a solid support suitable for a diagnostic assay (e.g., beads, plates, slides or wells formed from materials such as latex or polystyrene) in accordance with known techniques, such as precipitation. Antibodies which bind an ApoE isoform may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Kits for determining if a subject is or was afflicted with or is or was at increased risk of developing Alzheimer's disease will include at least one reagent specific for detecting for the presence or absence of ApoE4 and instructions for observing that the subject is or was afflicted with or is or was at increased risk of developing Alzheimer's disease if the presence of ApoE4 is detected. The kit may optionally include a nucleic acid for detection of the ApoE4 gene or instructions for isoelectric focusing methods for detecting ApoE4.

Diagnostic kits for carrying out antibody assays may be produced in a number of ways. In one embodiment, the diagnostic kit comprises (a) an antibody which binds ApoE2, ApoE3, or ApoE4 conjugated to a solid support and (b) a second antibody which binds ApoE2, ApoE3, or ApoE4 conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Immunochemical Methods for Detecting ApoE4

The novel immunochemical methods disclosed here can be easily carried out to detect and distinguish ApoE alleles in a subject for any purpose described herein or otherwise, whether screening subjects (e.g., diagnosing or prognosing) for Alzheimer's disease or screening subjects for cardiovascular disease.

The immunochemical assay comprises optionally (but preferably) combining a sample such as a blood sample collected from the subject with a reducing agent, then contacting the sample to a solid support which specifically binds reactive sulfhydryl groups, then separating the sample from the solid support; and then detecting by immunoassay either (i) the presence or absence of ApoE in said sample, the presence of ApoE in said sample indicating the subject has at least one allele for ApoE4, the absence of ApoE in said sample indicating said subject has no alleles for ApoE4, or (ii) the presence or absence of ApoE immobilized on the solid support, the presence of ApoE immobilized on said solid support indicating said subject has one or no alleles for ApoE4, the absence of ApoE immobilized on the solid support indicating said subject has two alleles for ApoE4.

Any sample of biological material containing ApoE may be used. For example, the sample may be collected from blood, blood serum, blood plasma, cerebrospinal fluid, or any other fluid or tissue containing ApoE from the subject.

It will be readily appreciated that the detecting steps described herein may be carried out directly or indirectly. Thus, for example, if either ApoE2 or ApoE3 is also detected in the subject, then it is determined that the subject is not homozygous for ApoE4; and if both ApoE2 and ApoE3 are detected in the subject, then it is determined that the subject is neither homozygous nor heterozygous for ApoE4. If either ApoE2 or ApoE3 is present the possibility exists that the individual is heterozygous for ApoE4. Heterozygosity for ApoE4 is also indicated if the amount of ApoE4 bound to the column is determined to be about twice the amount eluted from the column. Alternatively, to make further distinctions, the assay of the present invention can be used as an initial screen and combined with another assay capable of distinguishing between ApoE2, ApoE3, and ApoE4, such as an immunoassay, isoelectric focusing, or PCR analysis of DNA encoding ApoE2, ApoE3, and ApoE4.

Any solid support which specifically binds reactive sulfhydryl groups may be employed in carrying out the present invention. By specific, it is meant that the solid support will covalently bind sulfhydryl groups in the presence of competing groups such as amino, hydroxyl, and carboxylate. These solid supports include, but are not limited to, solid supports employing tresyl chemistry (K. Nilsson, *Methods. Enzymol.* 63, 56 (1984)), activated gels having pyridyl disulfide (T. Egorov et al., *Proc. Natl. Acad. Sci. USA* 72, 171 (1975)) or dithio-5-nitrobenzoic acid moieties that produce disulfide linkages, and TNB-thiol (5-thio-2-nitrobenzoic acid) agarose gels (e.g., Pierce product number 20409G, available from Pierce Chemical Co., Post Office Box 117, Rockford, Ill. 61105 USA). Preferred solid supports are those represented by the formula $R\text{-COCH}_2X$, wherein R is a solid substrate such as a gel and X is halogen (e.g., Cl, Br, I, preferably I). Particularly preferred is the SULFOLINK® coupling gel available as product numbers 44895G, 20405G, 20401G, 20402G, and 20403G from Pierce, Post Office Box 117, Rockford, Ill. 61105 USA.

Any agent capable of reducing the disulfide bond in cysteine residues to the corresponding reactive sulfhydryl groups may be used as the reducing agent to carry out the present invention. Preferably the reducing agent is a lower molecular weight thiol, more preferably mercaptoethanol, dithiothreitol, and mercaptoethylamine. Reduction of the disulfide bonds in cysteines will typically be carried out at slightly alkaline and denaturing conditions (for example, 8M urea or 6M guanidine HCl).

Once the sample has been contacted to the solid support, it is separated from the solid support by any known means and, if desired, collected for further testing.

The immunoassay step is carried out by specifically binding ApoE with an antibody which specifically binds to ApoE. The antibodies include all types of immunoglobulins, including IgG, IgM, IgA, IgD, and IgE produced by any known suitable method as described above.

An advantage of the foregoing technique is that it is not necessary to employ an antibody which binds specifically to one ApoE isoform without binding to one or more of the other isoforms. However, such isoform-specific antibodies may be employed if desired. Antibodies specific for ApoE are readily made and are known.

Immunoassays may, in general, be homogeneous assays or heterogeneous assays, as described above. As also described above, antibodies which specifically bind ApoE may be conjugated to a solid support suitable for a diagnostic assay (e.g., beads, plates, slides or wells formed from materials such as latex or polystyrene) in accordance with known techniques, and they may likewise be conjugated to detectable groups.

Diagnostic kits for carrying out the immunochemical assay may be produced in a number of ways. In one embodiment, the kit comprises (a) a solid support which specifically binds reactive sulfhydryl groups, (b) an antibody which binds to ApoE2, ApoE3, and/or ApoE4, and (c), optionally, a reducing agent. In another embodiment, the diagnostic kit comprises (a) an antibody which binds ApoE2, ApoE3, and/or ApoE4 conjugated to a solid support and (b) a second antibody which binds ApoE2, ApoE3, and/or ApoE4 conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

In brief, in a particular embodiment of the present invention, blood is collected and allowed to clot, and serum is removed. An aliquot of serum is placed into a reducing agent (e.g. dithiothreitol or β-mercaptoethanol) to reduce the cysteines, thereby producing reactive sulfhydryl groups. The reduced serum is then incubated with an activated support that reacts specifically and quantitatively with sulfhydryl groups (an example of this support is the SULFOLINK® coupling gel produced by Pierce Inc.). Incubation of reduced sera with this activated support will therefore bind all of the ApoE molecules which contain cysteine. After incubation, the serum containing unbound proteins is separated from the activated support with its bound proteins (either by sedimentation or by centrifugation). The serum is then assayed for the presence or absence of ApoE by an antibody specific for ApoE using an ELISA format, with one of several possible detection schemes (e.g. colorometric). ApoE2 or ApoE3 will quantitatively bind to the activated-support, and no free ApoE will be detected in the serum in the ELISA. ApoE4 will not bind to the activated-support, and will therefore be detected in the ELISA assay. Sera of a homozygote ApoE4 patient (containing only the ApoE4 isoform) will have about the same amount of ApoE in the sera after incubation with the activated-support as before incubation. Sera from a heterozygote ApoE4 patient (containing both ApoE4 and another ApoE isoform) will have approximately half the ApoE detected after incubation with the activated-support as before incubation.

The present invention is explained in greater detail in the following non-limiting Examples in which ml means milliliters, μl means microliters, and μg means micrograms.

EXAMPLE 1

Binding of Cerebrospinal Apolipoprotein E to Immobilized Beta-Amyloid Precursor Protein Fragments βA peptides (Bachem), other peptides, or ethanolamine were covalently immobilized to Immobilon AV affinity membrane (Millipore). The membrane is a chemically activated hydrophilic microporous membrane which covalently immobilizes peptides and proteins through amino and thiol groups. βA peptides, or control peptides, were dissolved in distilled water at one mg peptide/100 μL. Ten microliters (containing one hundred micrograms peptide) were applied to a 13 mm diameter Immobilon disc, and incubated to dryness overnight at room temperature. Peptide was in large excess to the number of functional binding groups on the membrane. Control membranes were prepared by incubating the membrane in 2.0M ethanolamine in 1.0M NaHCO$_3$, pH 9.5, to block the reactive groups on the Immobilon AV membrane. Membranes were stored at −20° C. in a desiccator. Prior to use the membranes were washed with phosphate buffered saline. The 12-28 Hydropathic Mimic Peptide and the Even-Hydro Peptide were synthesized using standard f-Moc synthesis on an Applied Bio-Science 430A peptide synthesizer. Amino acids were protected with blocking groups, and were deprotected and washed prior to manual cleavage. Purity of the peptides was verified by reverse phase high performance liquid chromatography.

Binding of CSF proteins to immobilized peptides.

Immobilon AV membranes previously bound with βA peptides, with ethanolamine, or with the hydromimic or even-hydro peptides were incubated with 100 μL cerebrospinal fluid (previously filtered through a 0.22μ filter) with 50 μL phosphate-buffered saline, pH 7.3, for thirty minutes at room temperature. After incubation the membranes were placed in a Millipore filter holder (Swinnex) and washed with 3.0 ml phosphate-buffered saline, then washed with 700 μL 5 % sodium dodecylsulfate (SDS). The membranes were removed from the filter holder, cut in half and placed in 150 μL of Laemmli buffer (2% sodium dodecylsulfate, 5% betamercaptoethanol, pH 6.8) and boiled five minutes to solubilize retained proteins. Forty-five μL of Laemmli buffer with solubilized protein were loaded in each of ten lanes of a Bio-Rad Minigel apparatus, with a stacking gel of 4%, and a separating gel of 12% polyacrylamide with 2% SDS.

Immunodetection of ApoE.

Electrophoresed proteins were transferred to Immobilon P using standard Western transfer techniques. After transfer the membrane was incubated in Blotto (5% dried milk in Tris buffered saline, pH 7.6, with 0.5% Tween-20 (Pierce)) at room temperature for one hour. The membrane was next incubated in rabbit—anti-human apolipoprotein E antibody at 1:1,000 dilution (kindly supplied by Dr. Joel Morrisett, Dept. of Medicine, Baylor college of Med., Houston, Tex.) in Blotto overnight at 4° C., then washed five times in Blotto. The membrane was exposed to goat—anti-rabbit secondary antibody conjugated with horse radish peroxidase at 1:10,000 dilution for one hour at room temperature, then washed seven times in Blotto. Horse-radish peroxidase was then visualized with Enhanced Chemiluminesce Detection kit (Amersham), and exposed to Hyperfilm ECL (Amersham).

Cerebrospinal fluid samples.

Cerebrospinal fluid was obtained from clinical diagnostic lumbar punctures performed on human subjects following informed consent, and stored at −80° C.

Results.

Cerebrospinal fluid contains many proteins which bind to immobilized βA peptide, and to a control peptide ("even-hydro peptide") after incubation and elution with phosphate buffered saline. FIG. 1, top, column 1. Among these retained proteins is apolipoprotein E, as shown in FIG. 1, bottom, column 1. Many of these proteins are eluted from both immobilized peptides by 5% sodium dodecyl sulfate, column 2; by 4 molar urea, column 3; or by 6 molar guanidine hydrochloride; column 4. Guanidine hydrochloride did not however elute apolipoprotein E from the $\beta A_{(1-28)}$ peptide, but eluted virtually all the apolipoprotein E previously bound to the control peptide, as shown in FIG. 1, bottom, column 4.

Figure 2:
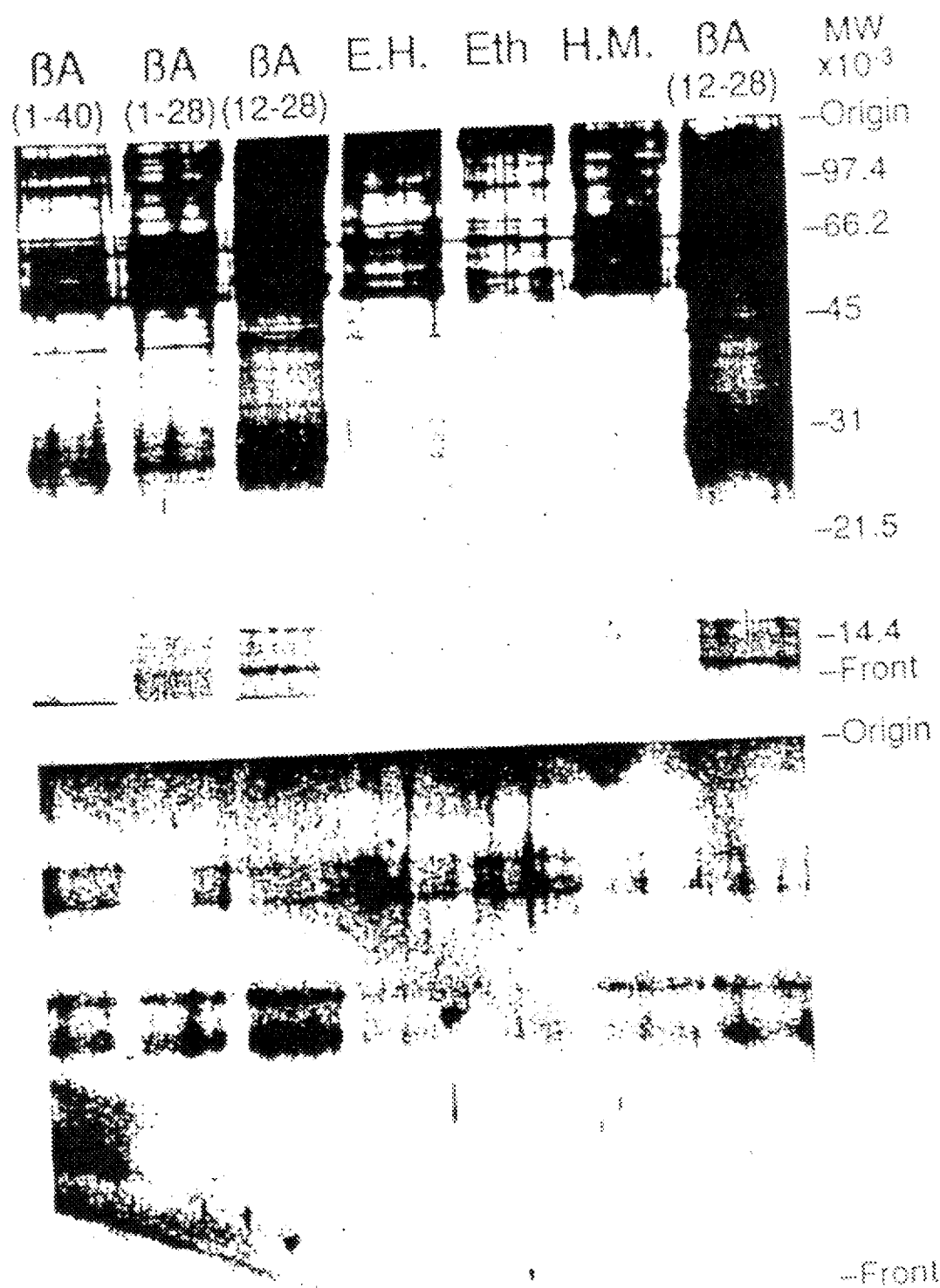
FIG. 2, top panel, shows the binding of proteins in cerebrospinal fluid to various immobilized peptides. Binding of Apolipoprotein E is again shown by immunohistochemical staining in the bottom panel.

The binding of apolipoprotein E to various immobilized peptides is shown in FIG. 2. Apolipoprotein E in cerebrospinal fluid binds with high affinity to immobilized $\beta A_{(1-40)}$, $\beta A_{(1-28)}$ and $\beta A_{(12-28)}$ following incubation and washing with PBS and 5% sodium dodecylsulfate. The "12-28 even hydro-peptide" contains the same amino acids as $\beta A_{(12-28)}$, but has a different hydropathic profile. Apolipoprotein E did not bind to this immobilized peptide, as shown in FIG. 2 bottom. The 12-28 hydropathic mimic peptide, contains different amino acids from $\beta A_{(12-28)}$, but has a hydropathy profile very similar to $\beta A_{(12-28)}$, and also bound apolipoprotein E.

EXAMPLE 2

Immunodetection of ApoE in CSF of Alzheimer's and Control Patients

Cerebrospinal fluid from both Alzheimer's disease patients, and control patients, contains immunoreactive apolipoprotein E. Apolipoprotein E in each control CSF bound to the immobilized $\beta A_{(1-28)}$. Apolipoprotein E in the Alzheimer's disease cerebrospinal fluid samples, however, demonstrated marked variability of binding to the $\beta A$ peptide.

EXAMPLE 3

Identification of ApoE Isoforms in Alzheimer's CSF by Isoelectric Focusing

To determine whether the variation in binding to the $\beta A$ peptide noted above could be explained by heterogeneity of the apolipoprotein E itself, CSF proteins were resolved by isoelectric focusing and immunoreactive apolipoprotein E was visualized. Cerebrospinal fluid (CSF) proteins were delipidated by agitation of 30 µL CSF with an equal volume of chloroform:methanol::2:1 (V/V). Delipidated CSF was then isoelectric focused using standard techniques on a urea, polacrylamide gel with Biorad ampholytes Ph 3–10 in a vertical slab gel apparatus (Biorad Minigel). Following electrophoresis, proteins were transferred to Immobilon P using Western technique and detected as described above. Several apolipoprotein E isoforms were detected by isoelectric focusing.

EXAMPLE 4

Detection of DNA Encoding the ApoE Type 4 Isoform in Blood Cells of Alzheimer's Disease Patients Population association studies of apolipoprotein E were carried out with over 85 blood samples from subjects afflicted with familial Alzheimer's disease, wherein the diagnosis of Alzheimer's disease was autopsy-proven.

Genomic DNA from the blood samples was extracted in accordance with standard techniques and amplified by polymerase chain reaction in either a Stratagene SCS-96 or Techne MW-2 thermocycler using Techne HI-TEMP 96 well plates and the primers described by P. Wenham et al., *Lancet* 337, 1158 (1991). The polymerase chain reaction protocol was essentially as described by Wenham et al. supra, and J. Hixson and D. Vernier, *J. Lipid Res.* 31, 545 (1990). Each amplification reaction contained 20 ng genomic DNA, 1.0 pmol/µL each primer, 10% dimethylsulfoxide (Sigma), 200 µL each dNTP (Pharmacia), 2.0 µCi (alpha-$^{32}$P) dCTP (800 Ci/mol in 10 mM Tricine, NEN Research Products) 0.05 Units/µL Taq DNA polymerase and supplied 1X incubation buffer (Boehringer Mannheim) in a final volume of 15 µL. An initial denaturation at 94° C. for 5 minutes was followed by 35 cycles of annealing at 65° C. for 0.5 minutes, extension at 70° C. for 1.5 minutes, denaturation at 94° C. for 0.5 minutes, and a final extension at 70° C. for 10 minutes. After amplification, 5 units of HhaI (Pharmacia) were directly added to each well, and the plates were incubated at least 3 hours at 37° C. Three µL of each reaction were loaded on a 6% nondenaturing gel (0.4 mm thick×43 cm long) and electrophoresed for one hour under constant current (45 mA). After electrophoresis, the gel was transferred to Whatman 3M chromatography paper, dried, and autoradiographed for one hour using Kodak XAR-5 film.

Data are given in Table 1 below. The results showed that the otherwise uncommon type 4 isoform was highly associated with Alzheimer's disease, compared to the normal population. The gene frequency of this type 4 isoform of apolipoprotein E in the general population is 16%, while in the Alzheimer's disease patients examined the gene frequency was 51%.

TABLE 1

ApoE Isotype in Normal and Alzheimer's Disease Patients.

| Apolipoprotein E Isotype (each chromosome) | Patient Population | |
|---|---|---|
| | Alzheimer's Disease | Normal |
| 2/2 | 0% | 1% |
| 3/3 | 20.7% | 60% |
| 4/4 | 24.4% | 3% |
| 2/3 | 3.6% | 12% |
| 2/4 | 3.6% | 2% |
| 3/4 | 47.6% | 23% |

These data indicate that detection of DNA encoding the type 4 isoform of apolipoprotein E is useful as a prognostic and diagnostic test for familial Alzheimer's disease.

EXAMPLE 5

Association of ApoE4 with Both Late-Onset Familial and Sporadic Alzheimer's Disease These data further support the involvement of the ApoE4 allele (ApoE-e4) in the pathogenesis of late-onset familial and sporadic AD.

Families.

Blood samples for the genomic DNA studies were obtained from families described previously (J. Murrell et al., *Science* 254, 97–99 (1991); H. Karlinsky et al., *Neurology* 42, 1445–1453 (1992); P. St. George-Hyslop et al., *Nature Genet.* 2, 330–334 (1992); M. Pericak-Vance et al., *Am. J. Hum. Genet.* 48, 1034–1050 (1991); and P. St. George-Hyslop et al., *Nature* 347, 194–197 (1990)). All sampled individuals diagnosed as probable Alzheimer's disease patients (AD) were examined by a neurologist and associated diagnostic personnel of the Joseph and Kathleen Bryan Alzheimer's Disease Research Center (ADRC) Memory Disorders Clinic at Duke University, the Centre for Neurodengenerative Diseases at the University of Toronto, or the Departments of Neurology at Massachusetts General Hospital and the Harvard Medical School. The clinical diagnosis was made according to the NINCDS-ADRDA criteria (C. McKhann et al., *Neurology* 34, 939–944 (1984)). The Duke pedigrees were primarily late-onset AD families with an average age of 66.1±10.3 years in the 35 families. Three of the families could be classified as early-onset (M<60 years) AD families. One family segregates with the APP717valile mutation (A. Goate et al., *Nature* 349, 704–706 (1991)), a second segregates with the APP717val-phe mutation (J. Murrell et al., *Science* 254, 97–99 (1991)), and the other is linked to chromosome 14 markers with a maximum lod score of 3.5 (G. Schellenberg et al., *Science* 258, 668–671 (1992) and P. St. George-Hyslop et al., *Nature Genet* 2, 330–334 (1992)). The Toronto pedigrees were classified as primarily early-onset families (13 of the 17 families). Five of the families were linked to chromosome 14 with lod scores greater than 3.0 in each family (P. H. St. George-Hyslop et al., *Nature Genet* 2, 330–334 (1992)) while a sixth pedigree had the APP17valile mutation (H. Karlinsky et al., *Neurology* 42, 1445–1453 (1992)). The family and genotypic data were processed via the PEDI-GENE™ system (C. Haynes et al., *Genet. Epidemiol.* 3, 235–239 (1986)).

Genomic DNA from some patients diagnosed as sporadic cases of probable AD at Duke, Toronto, and Boston have been banked over the past six years. Sporadic AD patients were defined as those without a known family history of AD or dementia. The sporadic, probable AD patients represented all of the banked DNAs in the Toronto and Duke banks as of November 1992, except for an ongoing prospective series begun in August 1992 at the Bryan ADRC Memory Disorders clinic. The DNA from these individuals had been collected randomly prior to any interest in ApoE isotyping. Not all sporadic AD patients evaluated in these clinics were banked routinely. The diagnosis of probable AD in this group can be expected to be in the 80–90% accuracy range that is observed in most specialized AD clinics. Brain DNA was obtained from autopsy-confirmed, Caucasian cases of AD that had been banked in the Kathleen Bryan Brain Bank at Duke, the University of Toronto, and the Harvard Medical School. Six black or American Indian autopsies were eliminated from the series of sporadic AD autopsies since the association analyses are sensitive to the control group. Two sets of controls were used in the study. The first set was 91 unrelated grandparents from the Centre d'Etude du Polymorphisme Humain (CEPH) reference families (J. Dausett et al., *Genomics* 6, 575–577 (1990)). These families were collected for human gene mapping and are characterized by having grandparents, parents, and many grandchildren available for DNA mapping. The grandparents represent a random group of Caucasian aged-controls of European and American background, similar to the late-onset FAD families and the autopsy-confirmed sporadic AD population. Twenty-one Caucasian spouses of patients participating in an ongoing prospective analysis of probable AD patients and spouses were also used as control group.

Genomic DNA.

High molecular weight DNA was obtained from transformed lymphoblasts according to know techniques (M. Pericak-Vance et al., *Neurology* 36, 1418–1423 (1986) and M. Pericak-Vance et al., *Exp Neurol* 102 271–279 (1988)) or to the GENEPURE 341™ nucleic acid extractor's supplied protocol (Applied Biosystems). Genomic DNA from brain tissue was isolated by pulverizing approximately 300 mg of frozen brain tissue under liquid nitrogen, adding 4 ml of lysis buffer (Applied Biosystems) and 1 mg of proteinase K (Applied Biosystems), and gently rocking overnight at 37° C. before extracting on the GENEPURE 341.

Amplification and restriction isotyping of ApoE.

Genomic DNA was amplified by polymerase chain reaction (PCR) in a Techne MW-2 thermocycler using HI-TEMP 96-well plates (Techne) and the primers described by P. Wenham et al., *Lancet* 337, 1158–1159 (1991). The PCR protocol was based on those described by Wenham et al. and J. Hixson et al., *J. Lipid Res.* 31, 545–548 (1990). Each amplification reaction contained 20 ng genomic DNA, 1.0 pmol/μl each primer, 10% dimethylsulfoxide (Sigma), 200 μm each DNTP (Pharmacia), 1.0 μCi (alpha-$_{32}$P) dCTP (800 Ci/mol in 10 mM Tricine, NEN Research Products), 0.05 units/μl Taq DNA polymerase and supplied 1X buffer (Boehringer Mannheim) in a final volume of 15 μl. An initial denaturation at 94° C. for 5 minutes was followed by 35 cycles of annealing at 65° C. for 0.5 minutes, extension at 70° C. for 1.5 minutes, denaturation at 94° C. for 0.5 minutes, and a final extension at 70° C. for 10 minutes. After amplification, 5 units of HhaI (Gibco) were directly added to each well, and the plates were incubated at least 3 hours at 37° C. Fifteen μL of 2X Type III stop dye (J. Sambrook et al., *Cold Spring Harbor Laboratory Press* B.24 (1989)) were added to each well, and 3 μL of each reaction were loaded on a 6% nondenaturing polyacrylamide gel (0.4 mm thick×43 cm long) and electrophoresed for one hour under constant current (45 mA). After electrophoresis, the gel was transferred to Whatman 3M chromatography paper, dried, and autoradiographed for one hour using Kodak XAR-5 film. Each autoradiograph was read independently by two different observers.

Statistical analysis.

Allele frequencies for the control and AD groups were estimated by counting alleles and calculating sample proportions. Allele frequency estimates for the early- and late-onset FAD families were calculated using one randomly selected affected patient from each family. The Z statistic for comparing two proportions was calculated (R. Elston and W. Johnson, *Essentials of Biostatistics*, (1987) and G. Schellenberg et al., *J. Neurogenet.* 4, 97–108 (1987)). An extreme value of Z compared to the probabilities for the standard normal distribution would suggest rejecting the null hypothesis that the allele frequencies in the two groups are equal. In order to compare the ApoE allele frequencies in the different populations, i.e., AD versus controls, and between control groups, the following comparisons were made: 1) CEPH controls versus spouse controls; 2) CEPH controls versus literature controls; 3) CEPH controls versus late-onset; 4) CEPH controls versus early-onset; 5) CEPH controls versus clinical (probable) sporadic AD; and 6) CEPH controls versus autopsy-confirmed sporadic AD. Affected-pedigree-member (APM) linkage analysis for ApoE was analyzed in accordance with known techniques (M. Pericak-Vance et al., *Am. J. Hum. Genet.* 48, 1034–1050 (1991) and D. Weeks et al., *Am. J. Hum. Genet.* 42, 315–326 (1988)). Two point lod scores were calculated using the computer program LINKAGE® Program Package (version 5.0) (G. Lanthrop et al., *Am. J. Hum. Genet.* 36, 460–465 (1984) and G. Lanthrop et al., *Proc. Natl. Acad. Sci. USA* 81, 3443–3446 (1984)). The age-of-onset and disease parameters used in the lod score calculations were as formerly outlined (M. Pericak-Vance et al., supra).

Results.

Table 2 illustrates the ApoE e4 allele frequency estimates in three control populations: 1) 91 grandparents from the CEPH reference families; 2) 21 spouses from an ongoing prospective study examining consecutive sporadic, probable AD patients, and 3) a representative control series from a similar population in the literature (G. Lanthrop et al., *Proc.*

Natl. Acad. Sci. USA 81, 3443-3446 (1984)). Also illustrated are the ApoE e4 allele frequency estimates for several different Alzheimer's disease groups: 1) one randomly selected affected individual in the combined Duke and Toronto/Boston late-onset FAD series; 2) one randomly selected affected individual in the combined Toronto/Boston and Duke early-onset FAD families; 3) banked DNA samples from sporadic patients carrying the diagnosis of probable AD from the Duke and Toronto/Boston clinics; and 4) DNA from 176 autopsy-confirmed sporadic AD patients from Duke and Toronto/Boston.

TABLE 2

ApoE-e4 Allele Frequency Estimates

| Population | e4 Allele[1] | Z[2] | P Value |
|---|---|---|---|
| Normal Controls | | | |
| CEPH[3] (182) | 0.16 ± 0.027 | | |
| Spouses[4] (42) | 0.10 ± 0.046 | 0.59 | 0.56 |
| Menzel[5] (2000) | 0.14 ± 0.008 | 0.71 | 0.48 |
| Alzheimer's Disease (AD) | | | |
| LOAD[6] (72) | 0.42 ± 0.058 | 4.30 | 0.000017 |
| EOAD[7] (32) | 0.19 ± 0.069 | 0.40 | 0.069 |
| Clinical Sporadic | | | |
| AD[8] (138) | 0.36 ± 0.042 | 4.17 | 0.00031 |
| Autopsy Sporadic | | | |
| AD[9] (352) | 0.40 ± 0.026 | 6.49 | <0.00001 |

[1] Allele frequency estimates ± the standard error; number of chromosomes counted is presented in parentheses.
[2] Z values are versus the CEPH control group.
[3] 91 unrelated grandparents from the Centre D'Etude du Polymorphism Humain (CEPH).
[4] Spouse controls in the Bryan ADRC Memory Disorders Clinic, Duke University.
[5] Population in H. Menzel et al., Apolipoprotein E polymorphism and Coronary Artery Disease, Arteriosclerosis 3, 310–315 (1983).
[6] "LOAD" means Late Onset AD; One randomly selected affected from each of 32 Duke and 4 Toronto/Boston late-onset FAD families.
[7] "EOAD" means Early Onset AD; One randomly selected affected from each of 13 Toronto/Boston and 3 Duke early-onset FAD families.
[8] 39 Duke and 30 Toronto/Boston sporadic (probable) AD patients.
[9] 143 Duke and 33 Toronto/Boston autopsy-confirmed sporadic AD subjects.

Consistent with Examples 1–4 above, the ApoE e4 allele frequency of the randomly selected affected patients in the predominantly late-onset FAD families was significantly different from that of the CEPH controls; 0.50±0.06 versus 0.16±0.027 (allele frequency estimate±standard error, Z=2.44, P=0.014). Likewise, the combined Duke and Toronto/Boston late-onset FAD series presented here is significantly different from the CEPH controls (P=0.000017). The ApoE-e4 frequency of the combined early-onset FAD series from Toronto/Boston and Duke (0.19±0.069) did not differ significantly (P=0.069) from the frequency in the CEPH controls. Statistical analyses demonstrate highly significant differences in the ApoE-e4 allele frequencies in both sporadic (probable) AD (P=0.00031) and autopsy-confirmed sporadic AD (P<0.00001) when compared to the CEPH controls.

EXAMPLE 6

Relation of Amyloid Beta-Peptide Deposition to Apolipoprotein E Type in Post-Mortem Tissue In this Example, a series of brains from patients with sporadic late-onset AD of known ApoE genotype was examined to determine whether AD brains with an ApoE-e4 allele have a distinct pattern of amyloid deposition. Brains of patients homozygous for ApoE-e4 were found to contain increased vascular amyloid deposits and number and density of amyloid and neuritic plaques compared to ApoE e3 homozygotes. In immunocytochemical studies, β-peptide was significantly increased in those patients with one or two ApoE-e4.alleles. The three main ApoE genotypes studied (e3/3, e3/4, and e4/4) showed no statistically significant difference in sex, age of onset or duration of illness. Late-onset Ad cases associated with one or two ApoE-e4 alleles thus have a distinct neuropathological phenotype compared to cases homozygous for the ApoE-e3 allele.

Case selection.

143 autopsy-confirmed cases of late-onset Alzheimer's Disease (AD) meeting NIH and CERAD criteria (C. McKhann et al., Neurology 34, 939–944 (1984) and S. Mirra et al., Neurology 41, 479–486 (1991)) and without affected family members or other neurological disease were obtained through the Kathleen Bryan Brain Bank at Duke University and analyzed for ApoE genotype. These cases were banked between 1985 and 1992. The average age at death for these 143 cases was 77.2±8.9 years of age with average duration of illness 8.6+/–4.2 years, and 63% of the patients were women.

ApoE Genotyping.

Genomic DNA was obtained by isolating DNA from approximately 300 mg of frozen brain tissue from each case. ApoE genotyping for each patient was carried out as described above using amplification by polymerase chain reaction with ApoE primers and HhaI restriction isotyping with autoradiographic detection. ApoE genotyping demonstrated: 47 cases ApoE e3/3, 64 cases ApoE e3/4, 23 cases ApoE e4/4, 3 cases ApoE e2/3 and 6 cases ApoE e2/4.

Neuropathological analysis.

Information on age at death, duration of illness, gender, brain weight, presence of amyloid deposits in cerebral vessels (using congo red stain) and description of neuritic plague density and amount of neurofibrillary tangles (modified King's silver stain [B. Lloyd et al., J. Histotech 6, 155–156 (1985)]) were taken from the original neuropathological reports. Neuritic plaque counts were mentioned in 100 cases and neurofibrillary tangle counts in 95 cases. Each count represented a single microscopic field felt to be the most affected area in the section of that region. Plaques were counted with a 10x objective (field of 2.92 mm$^2$ while tangles were counted with a 20x object (field of 0.72 mm$^2$). Plaque counts were truncated at 100 per 10x field. All of this data had been entered into the patients medical record one to five years prior to ApoE genotype analysis.

Analysis of congo red stained material for vascular amyloid.

A subset of 53 patients was chosen by selecting in chronological order those cases with preexisting congo red stained slides. Selection ended when 17 patients with ApoE genotype e4/4 (of the 23 total patients); 20 patients with ApoE genotype e3/3 (of the 49 total patients); and 16 patients with ApoE genotype e3/4 (of the 65 total patients) had been chosen. Forty of the 53 autopsy reports specifically mentioned vascular amyloid and formed one set of blinded observations completed before genotyping. The presence of vascular amyloid was graded at three levels: no evident amyloid deposits (grade 0), trace amyloid deposits including one positive vessel (grade 1), and readily identifiable vascular amyloid (grade 2). In addition, congo red stained slides of frontal cortex and hippocampus including entorhinal cortex from all 53 cases were examined by three observers for vascular amyloid using the same grading system. These observations were analyzed independently and double-blind with average inter-rater agreement of 8.5%.

Immunocytochemical methods.

Paraffin blocks of hippocampal region, frontal lobe and parietal lobe were obtained for 7 cases of ApoE e4/4, 8 cases of ApoE e3/3, and 4 cases of ApoE e3/4. Selection of cases was random without knowledge of neuropathological report. 6–8 micron paraffin sections were cut and mounted on coated slides for immunocytochemistry. Sections were deparaffinized, treated with 90% formic acid for 3 minutes, washed and then incubated with monoclonal antibody for immunolocalization of amyloid β-peptide (antibody described in S. Ikeda et al., *Prog. Clin. Biol. Res.* 317, 313–323 (1989), gift of Drs. George Glenner and David Allsop). Sections were reacted in parallel with identical antibody dilution and enzymatic detection steps using the ABC method (Vectorstain, Burlingame, Calif.), and a coverslip was placed over Permount after dehydration. Semi-adjacent sections (untreated with formic acid) were used to demonstrate neuritic plaques with monoclonal antibody (dilution 1:1000) to 164 kd-neurofilament protein (SMI-34, Sternberger-Meyer Immunocytochemicals, Inc) and for ApoE using a polyclonal antibody (dilution 1:20,000) to human ApoE which recognizes ApoE2, ApoE3 and ApoE4 isoforms on Western blots (gift of Dr. Joel Morrisett, Baylor College of Medicine). Parallel controls were unstained in these experiments.

Analysis of immunocytochemical material.

Regions of maximum plaque density in each section were selected and graphical analysis was performed by drawing plaque outlines using a camera lucida onto a defined rectangle of 0.25 $mm^2$ divided into 160 equal grids. Any gridboxes containing all or any portion of an immunoreactive plaque were counted, and the total was divided to actual genotype. Inter-rate reliability is 85% with these methods, and variance between separate fields from the same section 15%. Representative fields were photographed with a Zeiss photomicroscope.

Statistical analysis.

Data were entered in a Statgraphics package and analysis of variance used to describe the relationships between variables. No significant differences existed between the main set of 143 cases, the subset of 53 cases, or the smaller subsets above of ApoE e3/3, e3/4, and e4/4 genotypes chosen for congo red or immunocytochemical analysis with regard to age at death, gender ratio or brair weight. For comparison of plaque and neurofibrillary tangle counts, Kruskal-Wallis one-way analysis was employed since observations did not fit a normal distribution.

Immunolocalization of β-peptide amyloid deposits in brains of sporadic AD Patients homozygous for ApoE e3 or e4.

Immunocytochemistry for β-peptide in brains of patients with sporadic late-onset AD demonstrated consistent differences between immunostained sections of cerebral cortex from ApoE e3/3 and ApoE e4/4 cases (data no shown). β-peptide immunoreactivity in the sections from ApoE e3/3 cases reveals minimal to absent vascular staining and faintly immunoreactive plaques while sections from ApoE e4/4 cases are darkly stained with abundant immunoreactive vessels on the cerebral surface and strongly immunoreactive plaques and vessels in the parenchyma. The difference is typically of such magnitude that β-peptide immunostained sections from ApoE e4/4 brains can be differentiated from sections from ApoE e3/3 brains without a microscope.

Immunolocalization of ApoE in brains AD patients homozygous for ApoE e3 or e4.

ApoE immunoreactivity was observed in cerebral vessels, neurons, glial cells, senile plaques and neurofibrillary tangles as described in previous reports (J. Diedrich et al., *J. Virol.* 65, 4759–4768 (1991); and Y. Namba et al., *Brain Res.* 541, 163–166 (1991)). Like β-peptide immunoreactivity, ApoE immunoreactivity is enhanced after formic acid treatment. There were no major differences in the localization or intensity of ApoE immunoreactivity in ApoE e3/3 cases compared to ApoE e4/4 (note that this polyclonal antiserum to ApoE detects both ApoE 3 and ApoE 4 isoforms). In particular, most larger cerebral vessels were ApoE immunoreactive in both ApoE e4/4 cases and in ApoE e3/3 cases.

Extent of vascular amyloid in e3/3, e4/4 and e3/4 ApoE genotypes—retrospective analysis of autopsy reports.

In 40 of the 53 cases, the presence or absence of vascular amyloid detected by congo red staining was clearly noted in the autopsy report. Retrospective grading of these autopsy reports for amount of vascular amyloid deposits revealed a significant association of vascular amyloid with number of ApoE e4 alleles (p<0.0001). Typically, no vascular amyloid was mentioned for ApoE e3/3 cases, trace vascular amyloid for e3/4 cases, and large amounts were observed in most e4/4 cases (Table 3.A.1 below).

Prospective analysis of congo red stained material.

To examine prospectively the extent of vascular amyloidosis in the total series of 53 cases, a double-blind review of congo red stained sections of hippocampus and frontal cortex was conducted. This analysis confirmed a highly significant association between the presence of congo red positive amyloid angiopathy and the dose of ApoE e4 allele in the 53 cases (Table 3.A.1). Such amyloidotic vessels were not necessarily present throughout a given cortical region in ApoE e4/4 homozygotes, but often predominated in the depths of sulci such as the hippocampal fissure.

Analysis of β-peptide immunoreactive vessels.

When sections from a subset of the series of 53 patients were immunoreacted for β-peptide and similarly rated, the same statistically significant association between the amount of vascular amyloid and the dose of ApoE e4 allele was found (Table 3.C.1). Amyloidotic vessels in ApoE e4 homozygotes included leptomeningeal vessels and large and small vessels in the cortical plate with surrounding plaque-like accumulation of amyloid (plaque-like angiopathy of Scholze [W. Scholze, *Z. Gesamte Neurol. Psych.* 162, 694–715 (1938)]).

Neuritic plaque number is increased in ApoE e4 homozygotes compared to ApoE e3 homozygotes.

In four out of five cortical regions, the average number of neuritic plaques in silver stained material was greater in ApoE e4 homozygotes than in ApoE-e3 homozygotes (Table 1.A.2). Kruskal-Wallis one-way analysis revealed that increased average neuritic plaque count was significantly associated with ApoE-e4 allele dose in three regions: frontal, temporal and parietal cortex and that the association bordered on significance in the CA1 subfield of hippocampus. Neuritic plaque counts did not correlate with duration of illness.

Neurofibrillary tangle counts are mildly increased in ApoE e4 compared to ApoE e3 homozygotes.

In all five of the cortical regions presented above, the average number of neurofibrillary tangles was greater in ApoE-e4 homozygotes compared to ApoE-e3 homozygotes (Table 3.A.3). The chance that all five regions would have increased average neurofibrillary tangle count in ApoE e4/4 cases compared to ApoE e3/3 cases is 3% (nonparametric paired sample test). The differences in average counts for each area are modest and not significant by Kruskal-Wallis test. However, the average neurofibrillary tangle count in each cortical region varies significantly (p<0.01) with duration of illness in the whole set of patients and in the ApoE genotype subsets. The increase in average neurofibrillary tangle counts in ApoE-e4 homozygotes is apparently accounted for by the upward trend in duration of illness associated with ApoE-e4.

Immunocytochemical analysis of amyloid deposition in sporadic AD cases.

The large increase in amyloid deposition noted in ApoE-e4 homozygotes compared with ApoE-e3 homozygotes with sporadic AD includes both vascular amyloid deposition and deposition in senile plaques. In order to confirm qualitatively and quantitatively these differences, a set of 7 patients homozygous for ApoE-e4 was compared to a set of 8 patients homozygous for ApoE-e3. Four heterozygotes (ApoE-e3/4) were also examined to determine possible ApoE dosage effects. Low power views of cerebral cortex reveal the typical difference in over-all β-peptide immunoreactivity observed in β-peptide immunoreacted cortical sections of ApoE e3 homozygotes compared to e4 homozygotes (date not shown). These differences are consistently found even when β-peptide immunostained sections from a given cortical region are searched for microscopic fields with maximum density of immunoreactive plaques. Plaques in ApoE e4/4 cases were more numerous, somewhat larger often including a vessel, and darker than those observed in ApoE e3/3 cases.

TABLE 3

Neuropathological and Immunochemical Characteristics of Patients with Sporadic AD

| ApoE GENOTYPE | e3/3 | e3/4 | e4/4 |
|---|---|---|---|
| Age at death: (yr) | 76.4 | 79.1 | 75.8 NS |
| Illness duration: (yr) | 7.7 | 8.5 | 9.0 p = .06 |
| A. DATA FROM AUTOPSY REPORTS | | | |
| 1. Congophilic amyloid angiopathy: Ave. grade (0 = none, 1 = trace, 2 = present) | | | |
| By Report: | 0.27 | 0.80 | 1.92 p < .0001 |
| By Review: | 0.40 | 1.16 | 1.76 p < .0001 |
|  | n = 20 | n = 16 | n = 17 |
| 2. Neuritic plaques: Ave. plaques per low power field w/10× objective (2.92 mm²) | | | |
| Frontal cortex | 59 | 81 | 87 p < .0003 |
| Temporal cortex | 62 | 77 | 87 p < .009 |
| Parietal cortex | 61 | 68 | 86 p < .007 |
| Entorhinal cortex | 27 | 30 | 25 p = .69 |
| Hippocampus (CA1) | 12 | 13 | 18 p = .13 |
|  | n = 30 | n = 48 | n = 22 |
| 3. Neurofibrillary tangles: Ave. number per high power field w/20× objective (0.72 mm²) | | | |
| Frontal cortex | 6 | 7 | 8 p = .34 |
| Temporal cortex | 7 | 9 | 13 p = .16 |
| Parietal cortex | 7 | 10 | 8 p = .15 |
| Entorhinal cortex | 31 | 35 | 42 p = .22 |
| Hippocampus (CA1) | 26 | 37 | 48 p = .07 |
|  | n = 28 | n = 46 | n = 21 |
| B. IMMUNOCYTOCEMICAL STUDIES | | | |
| 1. β-peptide immunoreactive vessels: Ave. grade (0 = none, 1 = trace, 2 = present) | | | |
|  | 0.50 | 0.50 | 2.00 p < .0001 |
|  | n = 8 | n = 4 | n = 7 |
| 2. β-peptide immunoreactive plaques: % area occupied | | | |
| Strongly immunoreactive | 4.5 | 9.4 | 31.7 p < .002 |
| Weakly immunoreactive | 12.9 | 4.0 | 6.1 p = .04 |
| Total plaques | 17.4 | 13.4 | 37.8 p < .008 |
|  | n = 8 | n = 4 | n = 7 |

Quantitative analysis of β-peptide immunoreactivity of plaques.

Sections of frontal cortex from fifteen cases of sporadic AD were immunoreacted for β-peptide localization and quantitative analysis was made of the microscopic fields containing maximum density of β-peptide immunoreactive plaques for each case (Table 3.B.2). There was a highly significant, seven-fold greater average area covered by strongly β-peptide immunoreactive plaques in ApoE e4/4 homozygotes compared to ApoE e3/3 homozygotes (p<0.002). ApoE e3/4 cases are intermediate.

In several ApoE e3/3 cases, weakly immunoreactive plaques were also present and their number was significantly higher than in ApoE e4/4 cases (p=0.04). Nevertheless, the average total area covered by all β-peptide immunoreactive plaques was two-fold greater (p<0.008) in ApoE e4/4 homozygotes compared to ApoE e3/3 homozygotes (Table 3.B.2).

Extent of neuritic plaques.

Additional semi-adjacent section of frontal cortex from eight of the above cases were immunostained with an antibody to neurofilament protein (SMI-34) to test whether neuritic plaque density varied between the ApoE-e3 and ApoE-e4 homozygotes. SMI-34 immunoreactivity reveals neuritic processes and neurons with neurofibrillary tangles. Neuritic plaques can be identified by their content of neuritic processes.

Although the number and total area covered by neuritic plaques (as defined by SMI-34 immunoreactivity) is less than that for amyloid plaques (as defined by β-peptide immunoreactivity) (data not shown), comparison of the plaque area measurements in semi-adjacent sections shows a significant and linear correlation for the two methods of plaque detection in these eight cases (p<0.006, r=0.73). The area covered by neuritic plaques is also significantly greater in ApoE-e4 homozygotes than in ApoE-e3 homozygotes (p<0.02).

EXAMPLE 7

Relationship of ApoE4 Gene Dose and Risk of Alzheimer's Disease

This Example quantifies both the increased risk for AD and earlier age at onset conferred by ApoE4 alleles in late onset AD families. Risk increased from 20% to 90% and mean age at onset decreased from 84 to 68 years with increasing number of ApoE4 alleles. These data indicate that ApoE4 gene dose is a major risk factor for late onset AD, and that homozygosity for ApoE4 is virtually sufficient to cause AD by age 80.

Four of the 46 families tested to date are early onset families; two have chromosome 21 APP mutations, and two are linked to chromosome 14. The frequency of ApoE4 was not elevated in these families. Members of 42 late onset families diagnosed with AD or examined and found to be unaffected after age 60, with known ApoE genotype, were evaluated. Before enrollment in our study, informed consent was obtained from each subject or, when necessary, their legal guardian. All study protocols were approved by the Duke University Medical Center Institutional Review Board. Descriptive statistics for affected and unaffected subjects are given in Table 4. On average, women survived longer than men, whether affected (p=0.02) or unaffected (p=0.13).

With regard to Table 4, note that more than 90% of clinically diagnosed cases were confirmed at autopsy. The predictive value of clinical examination is nearly 100% when a family member has an autopsy-confirmed diagnosis of AD. Four subjects with a diagnosis of AD and 30 subjects examined before age 60 were excluded from analysis. Late onset families were not linked to chromosome 21 or to chromosome 14 within 19% recombination of the region previously linked to early onset AD. The estimated maximum two-point LOD score for AD and ApoE was 2.61 at 6% recombination.

TABLE 4

Descriptive Statistics for Affected and Unaffected Subjects

| | Affected Subjects (n = 95) | | |
|---|---|---|---|
| | Age at Onset | | |
| | n | Mean | (SD) |
| Men | 34 | 71.8 | (8.4) |
| Women | 61 | 70.4 | (8.0) |
| | Unaffected Subjects (n = 139) | | |
| | Age at Death | | |
| | n | Mean | (SD) |
| Men | 62 | 77.7 | (8.0) |
| Women | 77 | 82.6 | (9.2) |

The proportion of affected individuals increased with the number of ApoE4 alleles from 20% of subjects with genotype 2/3 or 3/3, to 47% of subjects with genotype 2/4 or 3/4, and to 91% of subjects with the 4/4 genotype (Table 5). This additive trend was highly significant (chi-squared=33.4 with 1 df, p<0.00001) (G. Koch et al., *Analysis of Categorical Data* (Les Presses de L'Universite de Montreal, Montreal, 1985) and SAS Institute, Inc., *SAS/STAT Use's Guide*, Release 6.03 Edition (SAS Institute, Cary, N.C., 1988)). More women than men were affected (p=0.04). This suggests that women may possibly be at greater risk for AD.

TABLE 5

| Percent Affected for Each ApoE Genotype | | |
|---|---|---|
| ApoE Genotype | % Men Affected (n) | % Women affected (n) |
| 2/2 | — (0) | — (0) |
| 2/3 | 28.6 (7) | 11.1 (9) |
| 3/3 | 7.1 (28) | 28.6 (49) |
| 2/4 | 50.0 (2) | 0.0 (3) |
| 3/4 | 38.3 (47) | 54.5 (66) |
| 4/4 | 91.7 (12) | 90.9 (11) |

As shown in Table 6, risk of AD increased by a factor of 2.84 (95% confidence interval (CI) 2.03 to 3.96) for each additional ApoE4 allele (D. R. Cox et al., *Analysis of Survival Data* (Chapman and Hall, London, 1984) and L. Wei et al., *JASA* 84, 1065 (1989)). Hence, subjects with the 4/4 genotype were more than 8 times as likely to be affected as subjects with 2/3 or 3/3 genotypes. When separate estimates were made for subjects with 0, 1, and 2 ApoE4 alleles, there was consistent evidence (which did not reach statistical significance) that women were at higher risk than men. Risk for women over men was 1.33 (95% CI 0.42 to 4.26), 1.39 (95% CI 0.76 to 2.55), and 1.30 (95% CI 0.50 to 3.38) at 0, 1, and 2 ApoE4 gene doses, respectively.

TABLE 6

Percentage of Affected Subjects and Relative Hazard According to the Number of ApoE4 Alleles.

| ApoE4 GENE DOSE | Men | | Women | | Combined | | Hazard Ratio |
|---|---|---|---|---|---|---|---|
| | % Aff | (n) | % Aff | (n) | % Aff | (n) | |
| 0 | 11.4 | (35) | 25.9 | (58) | 20.4 | (93) | 1.00 |
| 1 | 38.8 | (49) | 52.2 | (69) | 46.6 | (118) | 2.84+ |
| 2 | 91.7 | (12) | 90.9 | (11) | 91.3 | (23) | 8.07+ |

Estimates of risk in Table 6 were derived by exponentiation of parameter estimates obtained from a Cox proportional hazard model which allowed risk to differ in men and women (SAS Institute Inc., *Analysis of Survival Data* (Chapman and Hall, London, 1984), and SAS Institute Inc., SAS Technical Report P-217, *SAS/STAT Software: The PHREG Procedure*, Version 6 (SAS Institute Inc., Cary, N.C., 1991)). The symbol "+" indicates that hazard was significantly different from the reference value of 1. Information on each subject between the ages of 60 and 75 was used as the assumption of proportional hazards did not hold after the diagnosis by age 75 of nearly all persons with 2 ApoE-e4 alleles. Statistically consistent, if not fully efficient, estimates of relative hazard result from proportional hazards models even when related individuals are evaluated (L. Wei et al., *JASA* 84, 1065 (1989)). Thus, estimates of risk closely approximate estimates which would have been found by sampling just one person from each of a much larger collection of families.

The Mantel-Haenszel correlation statistic (SAS Institute, Inc., *SAS/STAT User's Guide*, Release 6.03 Edition (SAS Institute, Cary, N.C., 1988), and D. R. Cox et al., *Analysis of Survival Data* (Chapman and Hall, London, 1984)), stratified by family, was used to evaluate the additive trend in risk with increasing ApoE4 gene dose. The proportion of affected subjects increased significantly with ApoE4 gene dose (chi-sq=33.4 with 1 d.f., p<0.00001).

Figure 3:
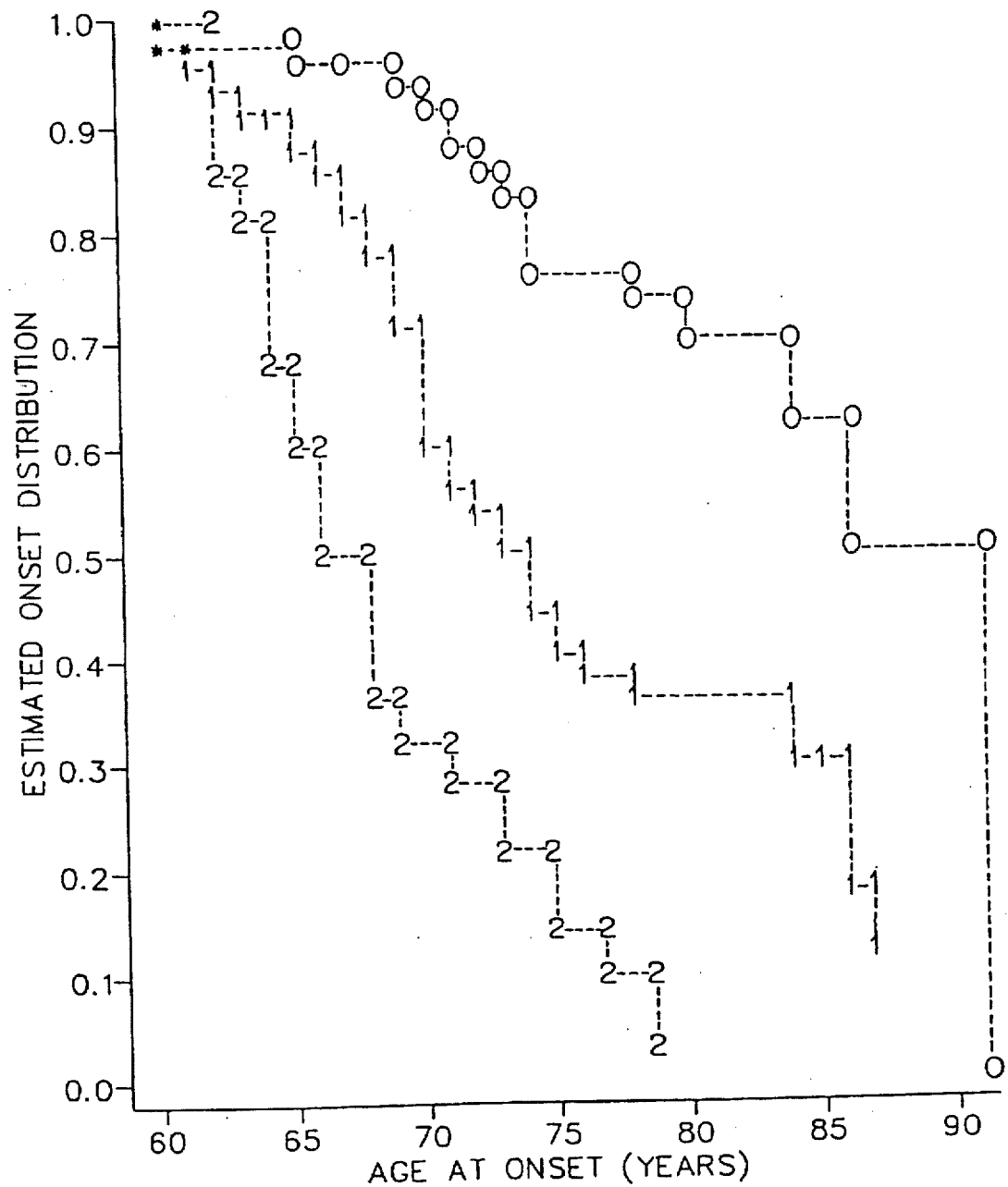
FIG. 3 shows the age at onset for subjects with 0, 1, and 2 ApoE4 alleles. Each curve is labeled by the number of ApoE4 alleles. The symbol '*' indicates multiple diagnoses within a short interval. Onset curves were estimated by Kaplan-Meier product limit distributions and were clearly distinct (logrank chi-square=53.8, 2 degrees of freedom, p<0.0001).

Next examined was age at onset to determine if it was related to ApoE4 gene dose. Onset distributions were constructed from information on age at onset in affected subjects and age when last examined in unaffected subjects and were distinct for each gene dose (chi-sq=53.84 with 2 d.f., p<0.00001) (R. G. Miller Jr., *Survival Analysis* (Whiley, New York, 1981), and SAS Institute Inc., SAS User's Guide: Statistics, Version 5 Edition (SAS Institute, Cary, N.C., 1985)) (FIG. 3). Each additional ApoE4 allele shifted onset to younger age; mean onset was 84.3 (SE 1.3) years in subjects with 1 ApoE4 allele, and 68.4 (1.2) years in subjects with 2 ApoE4 alleles. Onset tended to be earlier in women than in men (p=0.04).

Similarly, survival distributions were constructed from information on age at death in subjects known to be deceased and from age when last examined in other subjects, regardless of affection status. ApoE4 gene dose was related to survival (p=0.004); mean survival was 84.9 (SE 1.3) years in subjects with 0 ApoE4 alleles, 78.8 (SE 0.8) years in subjects with 1 ApoE4 allele, and 78.1 (SE 1.4) years in subject with 2 ApoE4 alleles. Earlier death in individuals with 1 or 2 ApoE4 alleles was primarily attributable to more frequent and earlier onset of AD in these subjects (p=0.001).

Despite shorter survival in subjects with 1 or 2 ApoE4 alleles, the earlier onset conferred by each ApoE4 allele leads us to suspect that most diagnoses of AD and most prevalent cases are in subjects with 1 or 2 ApoE4 alleles. The difference between mean onset and mean survival was 9.7 years in subjects with 2 ApoE4 alleles, 3.1 year in subjects with 1 ApoE4 allele and 0.6 years in subjects with 0 ApoE4 alleles.

Previous reports of linkage of AD to markers near the ApoE locus may have resulted from the allelic association of AD with ApoE4. Although these markers do not appear to be in disequilibrium with ApoE, their segregation could mimic linkage in families segregating at least one ApoE4 allele (D. A. Greenberg, *Am. J. Hum. Genet.* 52, 135-143 (1993)). The strong but not definitive evidence for linkage of AD to the ApoE locus (2=2.61, 0=0.06) also supports this explanation.

It is important to realize that 19 of 95 affected subjects in our cohort of pedigrees and 64 of 176 autopsy confirmed sporadic AD cases described by Saunders et al. (R. G. Miller Jr., *Survival Analysis* (Wiley, New York, 1981)) had no ApoE4 alleles. Twelve of 42 late onset families had affected members with 0 ApoE4 alleles. The fact that these tended to be the largest and based on simulation studies, the potentially most informative families for linkage, strongly suggests that other genetic sources of risk exist. These other genes will only be identified once the effects of the ApoE4 allele are included in subsequent analysis.

EXAMPLE 8

ApoE Isotyping Assay

400 µl of packed SULFOLINK® Resin (Pierce, Post Office Box 117, Rockford, Ill. 61105 USA) is washed with SULFOLINK® coupling buffer and resuspended in 2.0 ml of SULFOLINK® coupling buffer, all in accordance with the manufacturer's instructions in the Pierce IMMUNOPURE® Ag/Ab Immobilization Kit #2 (Pierce Catalog Number 44895G).

Four different assays were carried out, each in a 2 ml centrifuge column. Assay number 1 contained 180 µl of coupling buffer and 0.05 µg of purified human ApoE3. Assay number 2 contained 90 µl of resuspended SULFOLINK® resin and 0.05 µg of purified human ApoE3. Assay number 3 contained 180 µl of coupling buffer and 0.05 µg of purified human ApoE4. Assay number 4 contained 90 µl of resuspended SULFOLINK® resin and 0.05 Ag of purified human ApoE4.

Each assay was incubated at room temperature for 60 minutes. Each assay tube was then centrifuged 2 minutes in a desk top centrifuge and 30 µl of the supernatant was then withdrawn.

10 µl of Laemmli buffer (without β-mercaptoethanol) was added to each supernatant, and was placed in a well of a 12% polyacrylamide gel and electrophoresed. The proteins were then transferred by Western techniques and the ApoE identified by an antiApoE antibody and visualized using a secondary antibody and chemiluminescence detection, in accordance with known techniques (W. Strittmatter et al., *Proc. Natl. Acad. Sci. USA* 90, 1977-1981 (1993)).

Figure 4:
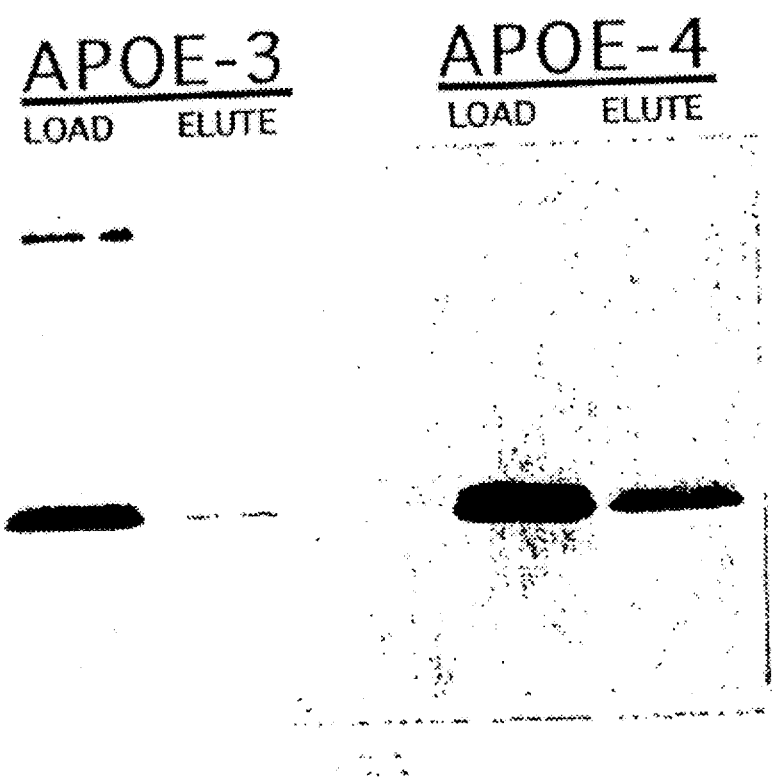
FIG. 4 shows the results of an assay of the present invention, where "load" refers to coupling buffer plus ApoE sample prior to combining with resin., and "elute" refers to the supernatant recovered from the assay after centrifugation.

Results are shown in FIG. 4, where "load" refers to the coupling buffer plus ApoE sample alone (assays 1 and 3) and "elute" refers to the supernatant recovered from the resuspended SULFOLINK® resin assays after centrifugation (assays 2 and 4). Note that ApoE4 is found in the elute, while ApoE3 is not, demonstrating that the assay is capable of distinguishing between ApoE3 and ApoE4.

The foregoing is illustrative of the present invention, and are not to be construed as limiting thereof. The invention is defined by the following claims, with equivalents of the claims to be included therein.

What is claimed is:

1. An apolipoprotein E isoform-specific monoclonal antibody, which antibody is selected from the group consisting of (i) a monoclonal antibody which specifically binds to the apolipoprotein E type 3 (ApoE3) isoform at the cysteine at amino acid position 112 and does not bind apolipoprotein E type 4 (ApoE4) isoform; and (ii) a monoclonal antibody which specifically binds to the ApoE4 isoform at the arginine at amino acid position 112 and does not bind the ApoE3 and the apolipoprotein E type 2 (ApoE2) isoforms.

2. An antibody according to claim 1, wherein said antibody specifically binds to the ApoE4 isoform.

3. An antibody according to claim 1 conjugated to a solid support.

4. An antibody according to claim 1 conjugated to a detectable group.

5. A monoclonal antibody according to claim 1, wherein said monoclonal antibody specifically binds the apolipoprotein E type 3 (ApoE3) isoform.

6. A monoclonal antibody according to claim 1, wherein said monoclonal antibody specifically binds the apolipoprotein E type 4 (ApoE4) isoform.

* * * * *